United States Patent [19]

Sisler et al.

[11] Patent Number: 5,518,988
[45] Date of Patent: May 21, 1996

[54] METHOD OF COUNTERACTING AN ETHYLENE RESPONSE IN PLANTS

[75] Inventors: Edward C. Sisler, Raleigh; Sylvia M. Blankenship, Apex, both of N.C.

[73] Assignee: North Carolina State University, Raleigh, N.C.

[21] Appl. No.: 253,951

[22] Filed: Jun. 3, 1994

[51] Int. Cl.⁶ .............................. A01N 3/02; A01N 27/00; A01N 29/04; A01N 33/04

[52] U.S. Cl. .................... 504/114; 504/115; 504/320; 504/326; 504/353; 504/356; 504/357

[58] Field of Search ..................................... 504/114, 115, 504/320, 326, 353, 356, 357

[56] References Cited

U.S. PATENT DOCUMENTS 3,879,188  4/1975  Fritz et al. ............................... 424/200
5,100,462  3/1992  Sisler et al. .............................. 71/121

OTHER PUBLICATIONS

M. C. Pirrung; *Proposal to the Fred C. Gioeckner Foundation* (1991).
Pirrung et al. "Ethylene Biosynthesis, Aminocyclopropene carboxylic acid", J. Chem. Soc., Chem. Commun., (13), 857–859, 1989.
Wheeler et al., "Synthesis of 1–aminocyclopropene carboxylic acid", J. Org. Chem., 52(22) 4875–4877, 1987.

*Primary Examiner*—Allen J. Robinson
*Assistant Examiner*—Brian G. Bembenick
*Attorney, Agent, or Firm*—Bell, Seltzer, Park & Gibson

[57] ABSTRACT

A method of inhibiting an ethylene response in a plant is disclosed herein. The method comprises applying to the plant an effective ethylene response-inhibiting amount of cyclopropene, 1.1.1. propellane, or derivatives thereof. Also disclosed are methods of inhibiting abscission in plants and methods of prolonging the life of cut flowers.

44 Claims, 4 Drawing Sheets

METHOD OF COUNTERACTING AN ETHYLENE RESPONSE IN PLANTS

This invention was made with government support under Grant No. 91-37304-65 awarded by the U.S. Department of Agriculture. The government has certain rights in the invention.

FIELD OF THE INVENTION

The present invention generally relates to plant growth regulation, and particularly relates to methods of inhibiting various ethylene responses by applying cyclopropene, 1.1.1. propellane, or derivatives thereof to the plant.

BACKGROUND OF THE INVENTION

Ethylene is known to mediate a variety of growth phenomena in plants. See generally Fritz et al. U.S. Pat. No. 3,879,188. This activity is understood to be achieved through a specific ethylene receptor in plants. Many compounds other than ethylene interact with this receptor: some mimic the action of ethylene; others prevent ethylene from binding and thereby counteract its action.

Many compounds which block the action of ethylene diffuse from the binding site over a period of several hours. See E. Sisler and C. Wood, *Plant Growth Reg.* 7, 181–191 (1988). These compounds may be used to counteract ethylene action. A problem with such compounds, however, is that exposure must be continuous if the effect is to last for more than a few hours.

Photoaffinity labeling has been used in biological studies to label binding sites in a permanent manner: usually by generating a carbene or nitrene intermediate. Such intermediates are very reactive and react rapidly and indiscriminately with many things. A compound already bound, however, would react mostly to the binding site. In a preliminary study, it was shown that cyclopentadiene was an effective blocking agent for ethylene binding. See E. Sisler et al., *Plant Growth Reg.* 9, 157–164 (1990). Methods of combatting the ethylene response in plants with diazocyclopentadiene and derivatives thereof are disclosed in U.S. Pat. No. 5,100,462 to Sisler and Blankenship.

SUMMARY OF THE INVENTION

The foregoing and other objects and aspects of the present invention are explained in detail in the specification set forth below.

A method of inhibiting an ethylene response in a plant is disclosed herein. The method comprises applying to the plant an effective ethylene response-inhibiting amount of cyclopropene or a derivative thereof.

Another aspect of the present invention is a method of blocking ethylene receptors in plants by applying cyclopropene or a derivative thereof to the plants in an effective receptor-blocking amount.

Also disclosed is a method of inhibiting abscission in a plant, comprising applying to the plant an effective abscission-inhibiting amount of cyclopropene or a derivative thereof.

Also disclosed is a method of prolonging the life of a cut flower, comprising applying to the cut flower an effective life-prolonging amount of cyclopropene or a derivative thereof.

The methods described herein may be carried out in any suitable manner, such as by contacting the plant to cyclopropene gas or a gas of a cyclopropene derivative, or by spraying the plant with a solution comprised of cyclopropene or a derivative thereof. These and other suitable methods of application are discussed in detail below.

A second method of inhibiting an ethylene response in a plant disclosed herein comprises applying to the plant an effective ethylene response-inhibiting amount of 1.1.1. propellane or a derivative thereof.

Another aspect of the present invention is a method of blocking ethylene receptors in plants by applying 1.1.1. propellane or a derivative thereof to the plants in an effective receptor-blocking amount.

Also disclosed is a method of inhibiting abscission in a plant, comprising applying to the plant an effective abscission-inhibiting amount of 1.1.1. propellane or a derivative thereof.

Also disclosed is a method of prolonging the life of a cut flower, comprising applying to the cut flower an effective life-prolonging amount of 1.1.1. propellane or a derivative thereof.

Yet another method of inhibiting an ethylene response in a plant is disclosed. The method includes applying to the plant an effective ethylene response-inhibiting amount of a compound isolated from light treated diazocyclopentadiene by Gas chromatography, wherein the compound elutes at about 0.7 minutes from a 23% SP-1700 on 80/100 Chromosorb P AW™ glass column.

The present invention also contemplates methods of blocking ethylene receptors in plants, inhibiting abscission in plants, and prolonging the life of cut flowers which include applying to the plant an effective ethylene response-inhibiting amount of a compound isolated from diazocyclopentadiene by Gas chromatography, wherein the compound elutes at about 0.7 seconds from a 23% SP-1700 on 80/100 Chromosorb P AW™ glass column.

DETAILED DESCRIPTION OF THE INVENTION

As noted above, in addition to cyclopropene and 1.1.1. propellane, various derivatives of cyclopropene and 1.1.1. propellane may also be used to carry out the methods set forth herein.

Derivatives of cyclopropene which may be used to carry out the present invention are defined by Formula (I) below:

wherein:

n is a number from 1 to 4. Preferably n is a number from 1 to 2, and most preferably n is 1.

R is selected from the group consisting of hydrogen, saturated or unsaturated $C_1$ to $C_4$ alkyl, hydroxy, halogen, alkoxy, amino and carboxy.

Derivatives of 1.1.1. propellane which may be used to carry out the present invention include those defined by Formula (II) below:

wherein n is from 1 to 3, preferably 1, and R is as defined above with reference to Formula (I).

R groups are preferably substituted on the compound of formula (II) on those carbon atoms which are covalently bound to two other carbon atoms, rather than those carbon atoms which are covalently bound to three other carbon atoms (i.e., to carbon atoms at the apexes of the structure shown).

The term "alkyl" as used herein refers to linear or branched, saturated or unsaturated alkyl. Examples include, but are not limited to, methyl, ethyl, propyl, isopropyl, and butyl. Alkyl groups of the present invention are preferably linear and saturated.

The term "plant" is used in a generic sense herein, and encompasses woody-stemmed plants such as trees and shrubs. Plants to be treated by the methods described herein include whole plants and any portions thereof, such as field crops, potted plants, cut flowers (stems and flowers), and harvested fruits and vegetables.

Plants treated by the methods of the present invention are preferably treated with a non-phytotoxic amount of the active compound.

The present invention can be employed to combat numerous different ethylene responses. Ethylene responses may be initiated by either exogenous or endogenous sources of ethylene. Ethylene responses include, for example, the ripening and/or senescence of flowers, fruits and vegetables, abscission of foliage, flowers and fruit, the prolongation of the life of ornamentals such as potted plants, cut flowers, shrubbery, and dormant seedlings, in some plants (e.g., pea) the inhibition of growth, and in other plants (e.g., rice) the stimulation of growth.

Vegetables which may be treated by the method of the present invention to inhibit ripening and/or senescence include leafy green vegetables such as lettuce (e.g., *Lactuea sativa*), spinach (*Spinaca oleracea*), and cabbage (*Brassica oleracea*), various roots, such as potatoes (*Solanum tuberosum*) and carrots (Daucus), bulbs, such as onions (*Allium sp.*), herbs, such as basil (*Ocimum basilicum*), oregano (*Origanum vulgare*), dill (*Anethum graveolens*), as well as soybean (*Glycine max*), lima beans (*Phaseolus limensis*), peas (*Lathyrus spp.*), corn (*Zea mays*), broccoli (*Brassica oleracea italica*), cauliflower (*Brassica oleracea botrytis*), and asparagus (*Asparagus officinalis*).

Fruits which may be treated by the method of the present invention to inhibit ripening include tomatoes (*Lycopersicon esculentum*), apples (*Malus domestica*), bananas (*Musa sapientum*), pears (*Pyrus communis*), papaya (*Carica papaya*), mangoes (*Mangifera indica*), peaches (*Prunus persica*), apricots (*Prunus armeniaca*), nectarines (*Prunus persica nectarina*), oranges (*Citrus sp.*), lemons (*Citrus limonia*), lines (*Citrus aurantifolia*), grapefruit (*Citrus paradisi*), tangerines (*Citrus nobilis deliciosa*), kiwi (*Actinidia chinenus*), melons such as cantaloupe (*C. cantalupensis*) and musk melon (*C. melo*), pineapple (*Aranas comosus*), persimmon (*Diospyros sp.*), various small fruits including berries such as strawberries (Fragaria), blueberries (*Vaccinium sp.*) and raspberries (e.g., *Rubus ursinus*), green beans (*Phaseolus vulgaris*), members of the genus Cucumis such as cucumber (*C. sativus*), and avocados (*Persea americana*).

Ornamental plants which may be treated by the method of the present invention to inhibit senescence and/or to prolong flower life and appearance (e.g., delay wilting), include potted ornamentals, and cut flowers. Potted ornamentals and cut flowers which may be treated with the present invention include azalea (*Rhododendron spp.*), hydrangea (*Macrophylla hydrangea*) hybiscus (*Hibiscus rosasanensis*), snapdragons (*Antirrhinum sp.*), poinsettia (*Euphorbia pulcherima*), cactus (e.g. *Cactaceae schlumbergera truncata*), begonias (*Begonia sp.*), roses (*Rosa spp.*), tulips (*Tulipa sp.*), daffodils (*Narcissus spp.*), petunias (*Petunia hybrida*), carnation (*Dianthus caryophyllus*), lily (e.g., *Lilium sp.*), gladiolus (*Gladiolus sp.*), alstroemeria (*Alstoemeria brasiliensis*), anemone (e.g., *Anemone blanda*), columbine (*Aquilegia sp.*), aralia (e.g., *Aralia chinensis*), aster (e.g., *Aster carolinianus*), bougainvillea (*Bougainvillea sp.*), camellia (*Camellia sp.*), bellflower (*Campanula sp.*), cockscomb (*celosia sp.*), falsecypress (*Chamaecyparis sp.*), chrysanthemum (*Chrysanthemum sp.*), clematis (*Clematis sp.*), cyclamen (*Cyclamen sp.*), freesia (e.g., *Freesia refracta*), and orchids of the family Orchidaceae.

Plants which may be treated by the method of the present invention to inhibit abscission of foliage, flowers and fruit include cotton (*Gossypium spp.*), apples, pears, cherries (*Prunus avium*), pecans (*Carva illinoensis*), grapes (*Vitis vinifera*), olives (e.g. *Vitis vinifera* and *Olea europaea*), coffee (*Coffea arabica*), snapbeans (*Phaseolus vulgaris*), and weeping fig (*ficus benjamina*), as well as dormant seedlings such as various fruit trees including apple, ornamental plants, shrubbery, and tree seedlings. In addition, shrubbery which may be treated according to the present invention to inhibit abscission of foliage include privet (*Ligustrum sp.*), photinea (*Photinia sp.*), holly (*Ilex sp.*) ferns of the family Polypodiaceae, schefflera (*Schefflera sp.*), aglaonema (*Aglaonema sp.*), cotoneaster (*Cotoneaster sp.*), barberry (*Berberis sp.*), waxmyrtle (*Myrica sp.*) abelia (*Abelia sp.*), acacia (*Acacia sp.*) and bromeliades of the family Bromeliaceae.

Additional ethylene responses include those listed in Fritz et al. U.S. Pat No. 3,879,188 at Column 3 line 62 through Column 6 line 65, the disclosure of which is incorporated herein by reference in its entirety.

The active compound of the present invention can be applied to plants by any suitable means. They may be applied alone, or in combination with inert carriers. The active compound may be applied alone in gaseous, liquid, or solid form, by contacting the compound to the plant to be treated. Additionally the active compound may be converted to the salt form, and then applied to the plants. Alternatively, the compound may be applied with a inert carrier. Suitable solid carriers include dust. The active compound may also be suspended in a liquid solution, as an organic solvent or an aqueous solution. Similarly, the gaseous form of the compound may be dispersed in an inert gaseous carrier to provide a gaseous solution.

Numerous organic solvents may be used as a carrier for the active compounds of the present invention, e.g., hydrocarbons such as hexane, benzene, toluene, xylene, kerosene, diesel oil, fuel oil and petroleum naphtha, ketones such as acetone, methyl ethyl ketone and cyclohexanone, chlorinated hydrocarbons such as carbon tetrachloride, esters such as ethyl acetate, amyl acetate and butyl acetate, ethers, e.g., ethylene glycol monomethyl ether and diethylene glycol monomethyl ether, alcohols, e.g., ethanol, methanol, isopropanol, amyl alcohol, ethylene glycol, propylene glycol, butyl carbitol acetate and glycerine.

Mixtures of water and organic solvents, either as solutions or emulsions, can be also employed as carriers for the active compound.

The active compounds can be applied as aerosols, e.g., by dispersing them in air by means of a compressed gas such as dichlorodifluoromethane or trichlorofluoromethane and other Freons, for example.

The active compounds of the present invention can also be applied with adjuvants or carriers such as talc, pyrophyllite, synthetic fine silica, attapulgus clay (attaclay), kieselguhr, chalk, diatomaceous earth, lime, calcium carbonate, bentonite, fuller's earth, cottonseed hulls, wheat flour, soybean flour pumice, tripoli, wood flour, walnut shell flour, redwood flour and lignin.

It may be desirable to incorporate a wetting agent in the compositions of the present invention. Such wetting agents may be employed in both the solid and liquid compositions. The wetting agent can be anionic, cationic or nonionic in character.

Typical classes of wetting agents include alkyl sulfonate salts, alkylaryl sulfonate salts, alkyl sulfate salts, alkylamide sulfonate salts, alkylaryl polyether alcohols, fatty acid esters of polyhydric alcohols and the alkylene oxide addition products of such esters, and addition products of long chain mercaptans and alkylene oxides. Typical examples of such wetting agents include the sodium alkylbenzene sulfonates having 10 to 18 carbon atoms in the akyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid (di-2-ethylhexyl), ester of sodium sulfosuccinic acid, sodium lauryl sulfate, sodium stearate and potassium oleate, sodium salt of the sulfonated monoglyceride of coconut fatty acids, sorbitan, sesquioleate, lauryl trimethyl ammonium chloride, octadecyl trimethyl ammonium chloride, polyethylene glycol lauryl ether, polyethylene esters of fatty acids and rosin acids, e.g., Ethofat 7 and 13, sodium N-methyl-N-oleyltaurate, Turkey Red oil, sodium dibutylnaphthalene sulfonate, sodium lignin sulfonate (Marasperse N), polyethylene glycol stearate, sodium dodecylbenzene sulfonate, tertiary dodecyl polyethylene glycol thioether (Nonionic 218), long chain ethylene oxide-propylene oxide condensation products, e.g., Pluronic 61 (molecular weight 1,000), sorbitan sesquioleate, polyethylene glycol ester of tall oil acids, sodium octyl phenoxyethoxyethyl sulfate, polyoxyethylene (20) sorbitan monolaurate ("Tween 20") tris (polyoxyethylene) sorbitan monostearate ("Tween 60"), and sodium dihexyl sulfosuccinate.

The solid, liquid, and gaseous formulations can be prepared by any of the conventional procedures. Thus, the active ingredient, in finely divided form if a solid, may be tumbled together with finely divided solid carrier. Alternatively, the active ingredient in liquid form, including solutions, dispersions, emulsions and suspensions thereof, may be admixed with the solid carrier in finely divided form.

The present invention is explained in greater detail in the following non-limiting Examples. In these examples, µl means microliters; ml means milliliters; l means liters, cm means centimeters; and temperatures are given in degrees Centigrade.

EXAMPLE 1

Isolation of Active Compound from Diazocyclopentadiene

Figure 1:
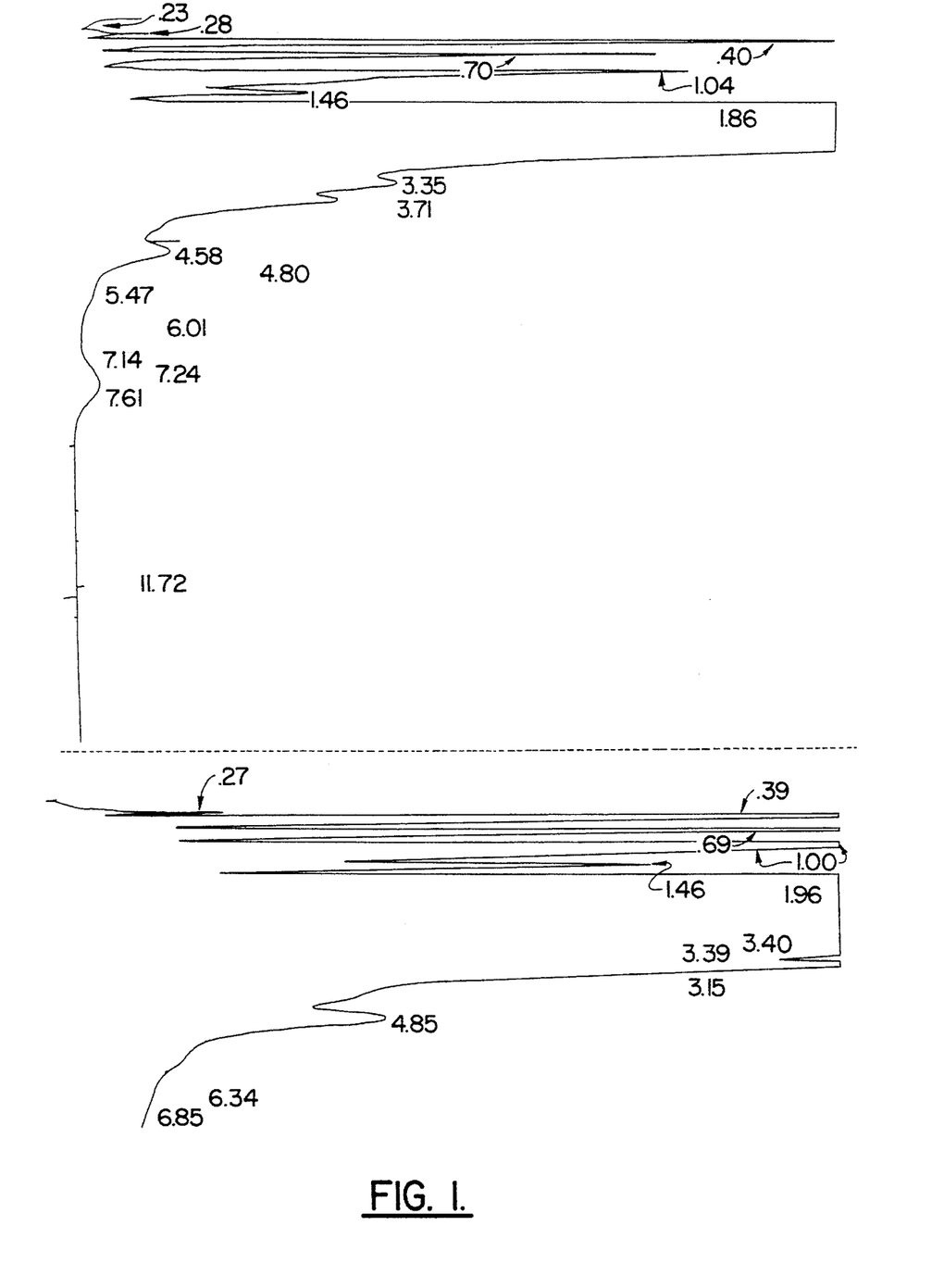
FIG. 1 is a gas-chromatograph, the peak at 0.70 illustrating an ethylene response-inhibiting compound isolated from diazocyclopentadiene.

Diazocyclopentadiene was placed in a glass container and exposed to light. A VARIAN™ Gas chromatograph equipped with a flame ionization detector and a 23% SP-1700 on 80/100 Chromosorb P AW™ glass column with nitrogen as a carrier gas was used to separate the mixture. Diazocyclopentadiene was analyzed at ambient temperature. A chromatogram was produced and the elution of each peak was timed using a stopwatch. An exemplary chromatogram is reproduced as FIG. 1.

Thereafter, the detector flame was extinguished and a piece of TYGON™ tubing was placed securely over the flame tip. The opposite end of the tubing was fitted with the hub of a syringe needle. Meanwhile, carnations were placed in glass jars containing water. Each peak was then permitted to elute into a separate jar. The procedure was repeated 5 times. Approximately 1 ml of pure oxygen was added to the jar to compensate for the reduction in the oxygen level due to the nitrogen carrier gas. The carnations were maintained overnight. The next day, the carnations were aired. Thereafter, the jars were resealed and ethylene gas was injected into the jars. The flowers were exposed to the ethylene atmosphere overnight. The next day the carnations were again aired and removed from the jars. Flowers were placed in water at room temperature until symptoms of senescence developed. Flowers that dried, closed up and showed typical ethylene injury symptoms were judged to be unprotected by a compound. Flowers that retained their fresh appearance were judged to be protected from the ethylene by the compound. The peak which eluted at about 0.70 minutes consistently protected the carnations from ethylene injury. The retention time on the column indicated that the active compound most likely contained 3 or 4 carbon atoms.

EXAMPLE 2

Measurement of Ethylene Binding

Triplicate samples of 3 g cut carnations' petals were placed in a 2.5l desiccator containing $^{14}$C-ethylene-mercuric perchlorate complex (110 mCi/mM) in a 25 ml Erlenmeyer flask. Then, an excess of unsaturated lithium chloride was added to the ethylene-mercuric perchlorate complex to release the gaseous ethylene. The mixture was stirred for 6 minutes. To determine the amount of binding, 3 ml of unlabelled ethylene was added in one desiccator. After 2 hours of ethylene exposure, the desiccators were opened and the samples were aerated for 4 minutes. Each sample was then placed in a 250 ml jar. 0.2 Ml of mercuric perchlorate on a 0.5 cm$^2$ piece of fiber-glass filter in a scintillation vial was then added. After 18 hours, the scintillation vials were removed, scintillation fluid added and the radioactivity counted for each sample.

EXAMPLE 3

Effect of 1-Methylcyclopropene and Dimethylcyclopropene in preserving in vivo carnations exposed to high levels of ethylene The treatment of carnations with ethylene hastens the process of senescence, producing a petal in-rolling phenomena (Halevy and Mayak, 1981). Carnations at stage II, with low ethylene production and no visible signs of senescence (Woodson, 1987) were treated with 1-methylcyclopropene at different concentration for 6 hours before adding 10 or 1000 ml/l of ethylene for 1 hour.

After 4 days, the carnations treated with only 2.5 nl/l of 1-methylcyclopropene looked like the control that did not have the ethylene treatment. The minimal concentration of 1-methylcyclopropene preventing the ethylene process was the same when flowers were treated with 1 ml/l of ethylene.

These results on in vivo carnations suggest that 1-methylcyclopropene acts as a potent inhibitor of ethylene response in the same way as STS, DACP or NBD. However, the concentration of 1-methylcyclopropene to protect the flower against ethylene action is much lower than these other chemical products.

EXAMPLE 4

Treatment time of 1-methylcyclopropene

Figure 2:
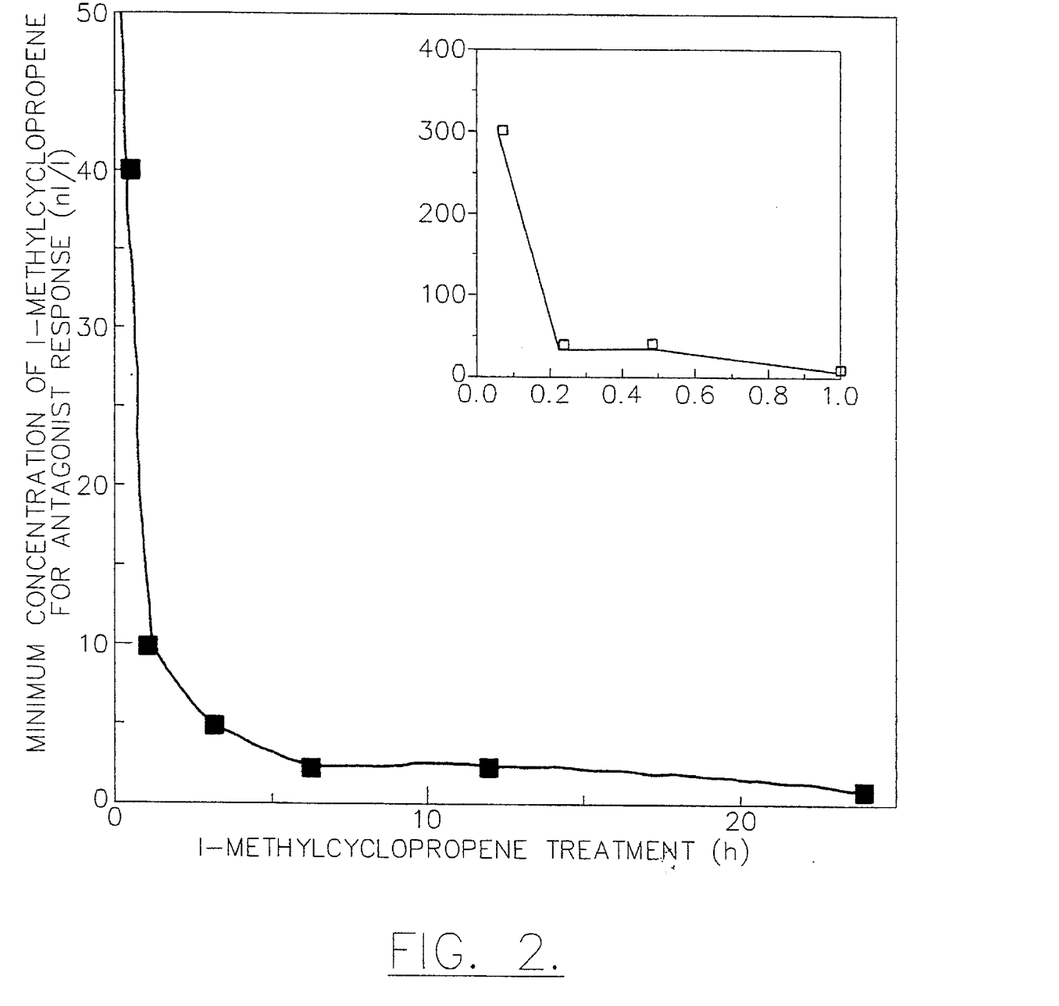
FIG. 2 shows a graph depicting the concentration of 1-methylcyclopropene needed to achieve protection against exogenous ethylene as a function of treatment time.

1-Methylcyclopropene was added for various times before the application of exogenous ethylene. FIG. 2 shows that the concentration of 1-Methylcyclopropene needed to get a protection against the effect of exogenous ethylene was inversely related to the treatment time. Treatment with about 250 to 300 nl/l of 1-methylcyclopropene for five minutes was enough to protect the flowers. Treated for 24 hours, with 0.5 nl/l protected against 1 ml/l of ethylene.

EXAMPLE 5

Irreversible binding of 1-methylcyclopropene on in vivo carnations

Flowers were treated with 5 nl/l of product during 6 hours, then, stored for 10 days at room temperature. One ml/l of ethylene was then added over 18 hours. Ethylene had no effect on the treated carnations 10 days after the 1-methylcyclopropene treatment (data not shown). The binding of 1-methylcyclopropene on carnations seems to be irreversible.

EXAMPLE 6

Effect of 1-methylcyclopropene on in vivo carnations to stop the senescent process due to exogenous and endogenous ethylene Flowers in a pre-senescent stage were treated with 5 nl/l of 1-methylcyclopropene and the senescent process was observed. An untreated control flower, began to exhibit petal in-rolling one day later (data not shown). The 1-methylcyclopropene treated flower did not show a senescent process 15 days later.

The carnations need to have an exogenous ethylene exposure at least for 6 hours to have a visible sign of senescence. Treatment with 3 nl/l of 1-methylcyclopropene is enough to stop that process. Carnations treated only with ethylene exhibited petal in-rolling, whereas carnations treated with ethylene and then 1-methylcyclopropene exhibited no visible sign of the phenomenon (data not shown). 1-methylcyclopropene seems to reduce and prevent the autocatalytic production of ethylene.

The ability of 1-methylcyclopropene to stop the senescence process was observed by adding ethylene over 6 hours. The carnations began to exhibit the in-rolling phenomena. Thereafter 1-methylcyclopropene was added. The process of senescence was stopped by the binding of 1-methylcyclopropene on the ethylene receptor and giving a molecular response.

EXAMPLE 7

Effect of 1-methylcyclopropene on ethylene production

Figure 3:
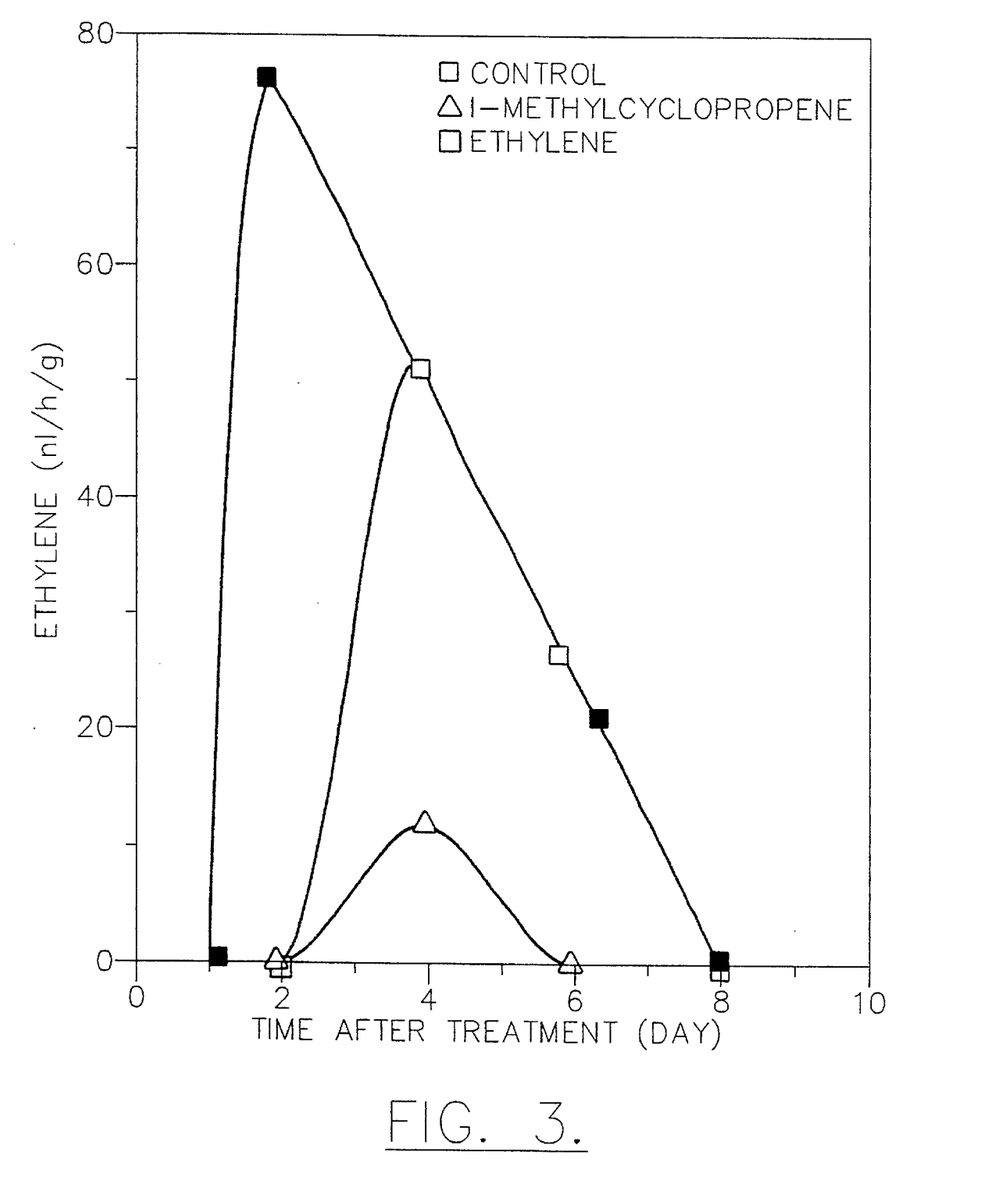
FIG. 3 compares the measurement of ethylene production in flowers treated with ethylene, with 1-methylcyclopropene, and untreated flowers.

Ethylene production was followed from the beginning of the ethylene climacteric production. The control exhibited a rise in ethylene production 4 days after beginning the experiment. Flowers first treated with ethylene, exhibited a rise in ethylene production 2 days earlier. 1- Methylcyclopropene was applied. Thereafter ethylene production was measured. As shown in FIG. 3, the measure of the ethylene production observed in the control was considerably lower than that observed in flowers treated with 1-methylcyclopropene.

EXAMPLE 8

Effect of 1-methylcyclopropene as a function of the stage of cut carnations

Cut carnations at stage I and stage III were treated with 1-methylcyclopropene. For young carnations, the concentration of 1-methylcyclopropene giving a protective effect was about 1.25 and 2.5 nl/l. For these, the protection against ethylene was total. For old carnations, rates between 2.5 and 5 nl/l of 1-methylcyclopropene were sufficient to give a response, but total protection was not achieved. Total protection of older carnations was only achieved with 10 nl/l of 1-methylcyclopropene (data not shown).

EXAMPLE 9

Irreversible binding of 1-methylcyclopropene on the ethylene receptor

Figure 4:
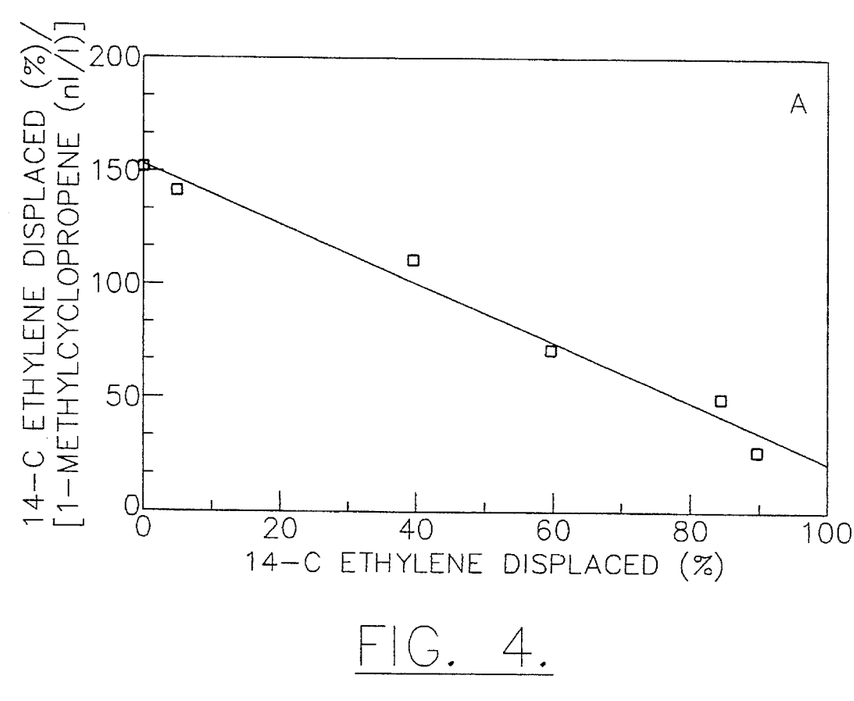
FIG. 4 shows the irreversible binding of the ethylene inhibitor on the ethylene receptor.

To determine if the 1-methylcyclopropene acted on the ethylene receptor, flowers were treated with 5 nl/l of 1-methylcyclopropene and stored for 4 days at room temperature at 4° C. before the ethylene binding experiment. Carnation petals preincubated with 1-methylcyclopropene and control petals which had not been incubated with 1-methylcyclopropene were then incubated in the presence of $^{14}$C-ethylene. One sample representing the control was incubated with a saturating concentration of unlabelled ethylene in the presence of $^{14}$C-ethylene. The difference in labelling of the 1-methylcyclopropene treated sample versus the non-treated sample and the control indicates the specific binding of ethylene. In the two cases, the ethylene binding was totally inhibited (see FIG. 4). Flowers treated with 1-methylcyclopropene did not bind ethylene.

EXAMPLE 10

Diffusion of $^3$H 1-methylcyclopropene on carnation petals

In order to label the ethylene receptor, 1-methylcyclopropene was labelled with tritium and the specific activity obtained was 60 mCi/mM. An eventual diffusion of the compound was studied on carnations. The flowers were treated with 1-methylcyclopropene, and with large amounts of ethylene. Control flowers were treated with 1-methylcyclopropene alone. The diffusion was followed for 7 days. Only the flowers which did not have the ethylene treatment showed a little diffusion. When the experiment was made at 4° C., the diffusion was nonexistent. These results suggest that $^3$H 1-methylcyclopropene was permanently bound to carnation tissues.

EXAMPLE 11

Effect of 1-methylcyclopropene on banana ripening

Bananas were individually placed in a 3 l jar. 1-Methylcyclopropene was injected into the jar at a determined concentration. The plant material was then aerated and 1 ml/l of ethylene was added for 12 hours. Controls were held in jars without chemical treatment. Chlorophyll measurement was made as previously described in Sisler and Wood, 1988). The experiment was done 7 days after 1-methylcyclopropene treatment.

The Ki obtained for chlorophyll disappearance was 40 ul/l when experiments were done in the dark and 1.2 ul/l when they were done in the light. The quantification of the effect of 1-methylcyclopropene was done by chlorophyll measurement. The Ki obtained for 1-methylcyclopropene was 0.4 nl/l. The ripening of 1-methylcyclopropene treated bananas was prevented for about 15 days and fruits turned brown after this period.

EXAMPLE 12

Effect of 1-methylcyclopropene tomato seed germination and tomato ripening

Tomato seeds were washed with NaOCl (10%) and rinsed with water. The seeds were placed on wetted filter paper with 10 mM sodium phosphate buffer at pH 5.8. The germination was done in the dark. When the seedlings were about 1 mm height, 30 seeds by sample were placed on wet filter paper in a 0.5 l jar. 1-Methylcyclopropene was added over 24 hours before adding 10 µl/l ethylene for 5 days.

When 1-methylcyclopropene was applied for 12 hours before the ethylene treatment, only 10 nl/l of compound was enough to preserve tomatoes. On these fruits, 1-methylcyclopropene had a temporary effect to prevent the ripening, which occurred about 7 to 10 days after the 1-methylcyclopropene treatment.

The foregoing is illustrative of the present invention and is not to be construed as limiting thereof. The invention is defined by the following claims, with equivalents of the claims to be included therein.

That which is claimed is:

1. A method of inhibiting an ethylene response in a plant, comprising applying to the plant an effective ethylene response-inhibiting amount of a compound of Formula I:

(I)

wherein:

n is the number 1; and

R is selected from the group consisting of hydrogen, saturated or unsaturated $C_1$ to $C_4$ alkyl, hydroxy, halogen, alkoxy, amino and carboxy.

2. A method according to claim 1, wherein n is 1.

3. A method according to claim 1, wherein said compound is cyclopropene.

4. A method according to claim 1, wherein said applying step is carried out by contacting said plant to a gas of said compound.

5. A method according to claim 1, wherein said applying step is carried out by spraying said plant with a solution comprising said compound.

6. A method according to claim 1, wherein said applying step is carried out by contacting said plant to a solid comprising said compound.

7. A method according to claim 1, wherein said ethylene response is fruit ripening.

8. A method according to claim 7, wherein said fruit is selected from the group consisting of tomatoes, apples, bananas, pears, papaya, mangoes, peaches, apricots, nectarines, kiwi, pineapple, persimmon, melons, pineapple, persimmon, berries, genus Cucumis, green beans and avocados.

9. A method according to claim 1, wherein said ethylene response is vegetable ripening.

10. A method according to claim 9, wherein said vegetable is selected from the group consisting of lettuce, spinach, cabbage, potatoes, carrots, onions, basil, oregano, dill, soybean, lima beans, peas, corn, broccoli, cauliflower, and asparagus.

11. A method according to claim 1, wherein said ethylene response is flower senescence.

12. A method according to claim 11, wherein said flower is selected from the group consisting of azalea, hydrangea, hibiscus, snapdragons, poinsettias, cactus, begonias, roses, tulips, daffodils, petunias, carnations, lily, gladiolias, alstromeria, anemone, columbine, avalia, aster, bouganvillea, camellia, bellflower, cockscomb, false cypress, chrysanthemum, clematis, cyclamen, freesia, and orchids.

13. A method of inhibiting abscission in a plant, comprising applying to the plant an effective abscission-inhibiting amount of a compound of Formula I:

(I)

wherein:

n is the number 1; and

R is selected from the group consisting of hydrogen, saturated or unsaturated $C_1$ to $C_4$ alkyl, hydroxy, halogen, alkoxy, amino and carboxy.

14. A method according to claim 13, wherein n is 1.

15. A method according to claim 13, wherein said compound is 1-methylcyclopropene.

16. A method according to claim 13, wherein said compound is cyclopropene.

17. A method according to claim 13, wherein said applying step is carried out by contacting said plant to a gas of said compound.

18. A method according to claim 13, wherein said applying step is carried out by spraying said plant with a solution comprising said compound.

19. A method according to claim 13, wherein said applying step is carried out by contacting said plant to a solid comprising said compound.

20. A method according to claim 13, wherein the plant is selected from the group consisting of cotton, apple, pear, cherry, pecan, grape, olive, coffee, snapbean, weeping fig, dormant seedlings, privet, photinea, holly, ferns, schefflera, aglaonema, cotoneaster, bar berry, waxmyrtle, abelia, acacia, and bromeliades.

21. A method of prolonging the life of a cut flower, comprising applying to the cut flower an effective life-prolonging amount of a compound of Formula I:

(I)

wherein:

n is a number from 1 to 2; and

R is selected from the group consisting of hydrogen, saturated or unsaturated $C_1$ to $C_4$ alkyl, hydroxy, halogen, alkoxy, amino and carboxy.

22. A method according to claim 21, wherein n is 1.

23. A method according to claim 21, wherein said compound is 1-methylcyclopropene.

24. A method according to claim 21, wherein said compound is cyclopropene.

25. A method according to claim 21, wherein said compound is 3,3-dimethylcyclopropene.

26. A method according to claim 21, wherein said applying step is carried out by contacting said plant to a gas of said compound.

27. A method according to claim 21, wherein said applying step is carried out by spraying said plant with a solution comprising said compound.

28. A method according to claim 21, wherein said applying step is carried out by contacting said plant to a solid comprising said compound.

29. A method of inhibiting an ethylene response in a plant, comprising applying to the plant an effective ethylene response-inhibiting amount of a compound of Formula I:

(I)

wherein:

n is a number from 1 to 2; and

R is selected from the group consisting of hydrogen, saturated or unsaturated C1 to C4 alkyl, hydroxy, halogen, alkoxy, and carboxy.

30. A method according to claim 29, wherein said compound is 3,3-dimethylcyclopropene.

31. A method of inhibiting an ethylene response in a plant, comprising applying to the plant an effective ethylene response-inhibiting amount of a compound of Formula I:

(I)

wherein:

n is a number from 1 to 2; and

R is selected from the group consisting of hydrogen, saturated or unsaturated $C_1$ to $C_4$ alkyl, hydroxy, halogen, alkoxy, and amino.

32. A method of inhibiting abscission in a plant, comprising applying to the plant an effective abscission-inhibiting amount of a compound of Formula I:

(I)

wherein:

n is a number from 1 to 2; and

R is selected from the group consisting of hydrogen, saturated or unsaturated $C_1$ to $C_4$ alkyl, hydroxy, halogen, alkoxy, and carboxy.

33. A method according to claim 32, wherein said compound is 3,3-dimethylcyclopropene.

34. A method of inhibiting abscission in a plant, comprising applying to the plant an effective abscission-inhibiting amount of a compound of Formula I:

(I)

wherein:

n is a number from 1 to 2; and

R is selected from the group consisting of hydrogen, saturated or unsaturated $C_1$ to $C_4$ alkyl, hydroxy, halogen, alkoxy, and amino.

35. A method of inhibiting an ethylene response in a plant, comprising applying to the plant an effective ethylene response-inhibiting amount of 1-methylcyclopropene.

36. A method according to claim 35, wherein said applying step is carried out by contacting said plant to a gas of said compound.

37. A method according to claim 35, wherein said applying step is carried out by spraying said plant with a solution comprising said compound.

38. A method according to claim 35, wherein said applying step is carried out by contacting said plant to a solid comprising said compound.

39. A method according to claim 35, wherein said ethylene response is fruit ripening.

40. A method according to claim 39 wherein said fruit is selected from the group consisting of tomatoes, apples, bananas, pears, papaya, mangoes, peaches, apricots, nectarines, kiwi, pineapple, persimmon, melons, pineapple, berries, genus Cucumis, green beans and avocados.

41. A method according to claim 35, wherein said ethylene response is vegetable ripening.

42. A method according to claim 41, wherein said vegetable is selected from the group consisting of lettuce, spinach, cabbage, potatoes, carrots, onions, basil, oregano, dill, soybean, lima beans, peas, corn, broccoli, cauliflower, and asparagus.

43. A method according to claim 35, wherein said ethylene response is flower senescence.

44. A method according to claim 43, wherein said flower is selected from the group consisting of azalea, hydrangea, hibiscus, snapdragons, poinsettias, cactus, begonias, roses, tulips, daffodils, petunias, carnations, lily, gladiolias, alstromeria, anemone, columbine, avalia, aster, bouganvillea, camellia, bellflower, cockscomb, false cypress, chrysanthemum, clematis, cyclamen, freesia, and orchids.

\* \* \* \* \*